(12) United States Patent
Martin

(10) Patent No.: US 6,237,159 B1
(45) Date of Patent: May 29, 2001

(54) HATS FOR GLASSES

(76) Inventor: William L. Martin, 7905 Spindletop Pl., Apt. 424, Charlotte, NC (US) 28277

( * ) Notice: Subject to any disclaimer, the term of this patent is extended or adjusted under 35 U.S.C. 154(b) by 0 days.

(21) Appl. No.: 09/440,670

(22) Filed: Nov. 16, 1999

Related U.S. Application Data

(60) Provisional application No. 60/124,741, filed on Mar. 17, 1999.

(51) Int. Cl.$^7$ .................................. A42B 1/00; A61F 9/00
(52) U.S. Cl. .......................... 2/290.12; 2/175.1; 2/195.1; 2/13
(58) Field of Search .............................. 2/15, 10, 12, 13, 2/175.1, 209.12, 195.1

(56) References Cited

U.S. PATENT DOCUMENTS

| | | | |
|---|---|---|---|
| 2,557,552 | * 6/1951 | Martin | 2/10 |
| 2,725,560 | 12/1955 | Feldman . | |
| 3,703,750 | * 11/1972 | Irwin, Jr. | 24/265 R |
| 4,179,753 | * 12/1979 | Aronberg et al. | 2/10 |
| 4,304,005 | 12/1981 | Danley, Sr. . | |
| 4,541,125 | 9/1985 | Phillips . | |
| 5,034,862 | * 7/1991 | Liston | 362/105 |
| 5,052,054 | 10/1991 | Birum . | |
| 5,117,510 | * 6/1992 | Broussard et al. | 2/209 |
| 5,129,102 | 7/1992 | Solo . | |
| 5,533,207 | 7/1996 | Diaz . | |
| 5,533,208 | 7/1996 | Tonoyan et al. . | |
| 5,867,874 | 2/1999 | Simpson . | |

FOREIGN PATENT DOCUMENTS 345833    4/1931  (GB) .

* cited by examiner

*Primary Examiner*—Bibhu Mohanty
(74) *Attorney, Agent, or Firm*—Richard C. Litman

(57) ABSTRACT

A baseball cap having mounting structure formed on its crown for securely supporting eye wear thereby preventing loss of the eye wear and rendering the eye wear easily accessible. In the preferred embodiment, the mounting structure takes on the form of pairs of aligned buttonholes on either side of the cap crown.

1 Claim, 2 Drawing Sheets

HATS FOR GLASSES

CROSS-REFERENCE TO RELATED APPLICATION

This application claims the benefit of U.S. Provisional patent application Ser. No. 60/124,741, filed Mar. 17, 1999.

BACKGROUND OF THE INVENTION

1. Field of the Invention

The present invention generally relates to wearing apparel. More specifically, the present invention is drawn to a baseball hat or cap having structure for retention of eye wear.

2. Description of the Related Art

The one piece of wearing apparel which seems to have attained universal appeal is the baseball cap. The baseball cap, often displaying sports team or company logos, is worn by males, females, young, and old. A great number of baseball cap aficionados also wear some type of eyeglasses (corrective lenses or shades). There are many instances when the eyeglass wearer may choose to remove the eyeglasses for a short period. The eyeglasses are usually laid aside and are often accidently broken or lost, thus necessitating expenditure of time and money for replacement. A convenient means to secure eyeglasses to a baseball cap would be a boon for the user, resulting in time and monetary savings.

There are many prior art devices for attaching eye wear to caps or hats. The attaching devices, however, all require relatively complicated structural mechanisms attached to the visor or brim. Such mechanisms are costly additions to the expense of the cap and are easily broken if the cap is accidently dropped or sat upon.

Examples of the above prior art devices are shown in U.S. Pat. No. 2,725,560 (Feldman), U.S. Pat. No. 4,304,005 (Danley, Sr.), U.S. Pat. No. 4,541,125 (Phillips), U.S. Pat. No. 5,129,102 (Solo), U.S. Pat. No. 5,533,207 (Diaz), and U.S. Pat. No. 5,553,208 (Tonoyan et al.).

U.S. Pat. No. 5,052,054 (Birum) and U.S. Pat. No. 5,867,874 (Simpson) show implement holding devices removably attached to caps. The devices of the instant patents require the user to be concerned with a separate mounting for the cap.

British Patent 345,833 shows a cap having means for detachably mounting the front of the cap to the peak. The patent does not disclose structure for supporting eye wear on the cap.

None of the above inventions and patents, taken either singly or in combination, is seen to disclose a cap having uncomplicated and efficient means for supporting eye wear as will be subsequently described and claimed in the instant invention.

SUMMARY OF THE INVENTION

The instant invention comprises a baseball cap structured to support a pair of eyeglasses when the glasses are not in use. The cap can be easily and quickly modified to form the support structure.

In the preferred embodiment, the support structure includes two buttonholes formed on each side of the cap. Each buttonhole is reinforced, as well known in the sewing art, to resist fraying. When a user removes his/her glasses, the end pieces and temples are simply inserted through the buttonholes. The glasses are, thus, securely mounted on the cap to prevent loss and to make them easily accessible when needed.

A second embodiment of the invention incorporates a sleeve disposed at each side of the cap. The temples of the glasses are inserted through the sleeves for support therein. This embodiment is effective for supporting glasses with straight end pieces.

A third embodiment of the invention employs the use of the cap's headband for securing the temples therein.

Although illustrated in conjunction with a baseball cap, it is obvious that the instant invention can be applied to head wear of other types.

Accordingly, it is a principal object of the invention to provide structure to mount and support eye wear on a cap.

It is another object of the invention to provide structure to support eye wear on a cap, which structure does not change the basic design or the style of the cap.

It is a further object of the invention to provide structure to support eye wear on a cap, which structure is easy to use.

Still another object of the invention is to provide structure to support eye wear on a cap wherein the eye wear is quickly accessible when needed.

It is an object of the invention to provide improved elements and arrangements thereof in an apparatus for the purposes described which are inexpensive, dependable and fully effective in accomplishing their intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
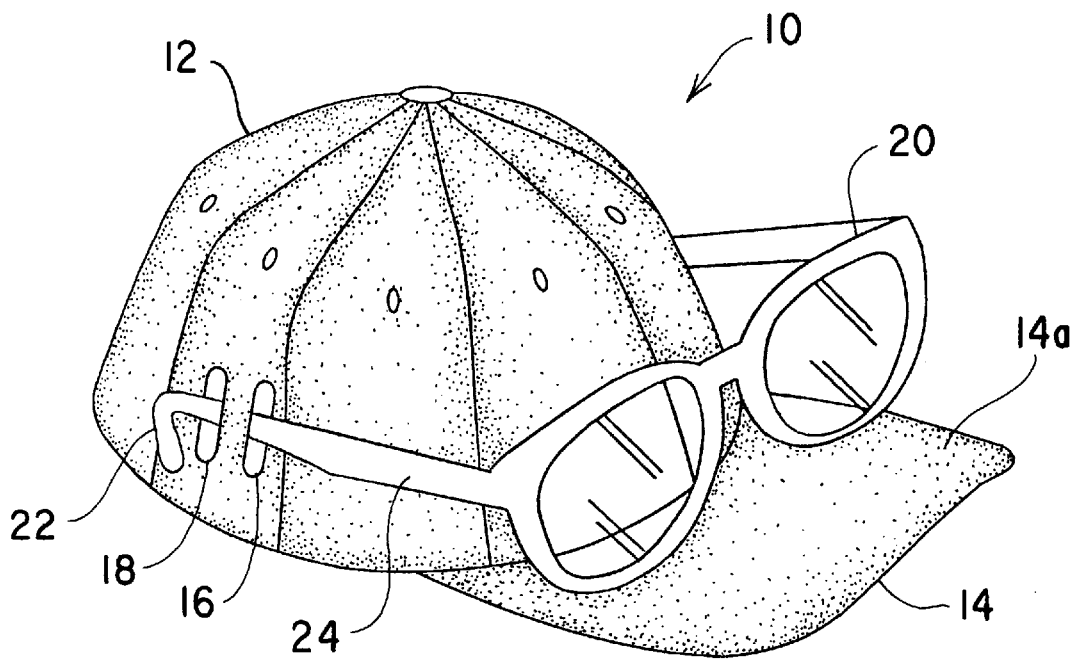
FIG. 1 is a perspective view of a hat for glasses according to a preferred embodiment of the present invention.

The cap of the preferred embodiment of the present invention is illustrated in FIG. 1 and is generally designated at 10. Cap 10 comprises a conventional body or crown 12 and visor 14. Disposed in each side of the crown 12 (only one side shown) are vertically oriented buttonholes 16 and 18 which are at least one-fourth of an inch in length. Buttonholes 16 and 18 are formed in the crown 12 in a conventional manner. The bottom of each buttonhole is approximately one and three-eights inches above the top surface 14a of the visor 14.

In use, end piece 22 and temple 24 of glasses 20 are simply inserted through the buttonholes on each side of the crown as shown. In this manner, glasses 20 can be quickly and securely mounted on the cap and are easily accessible when needed.

Figure 2:
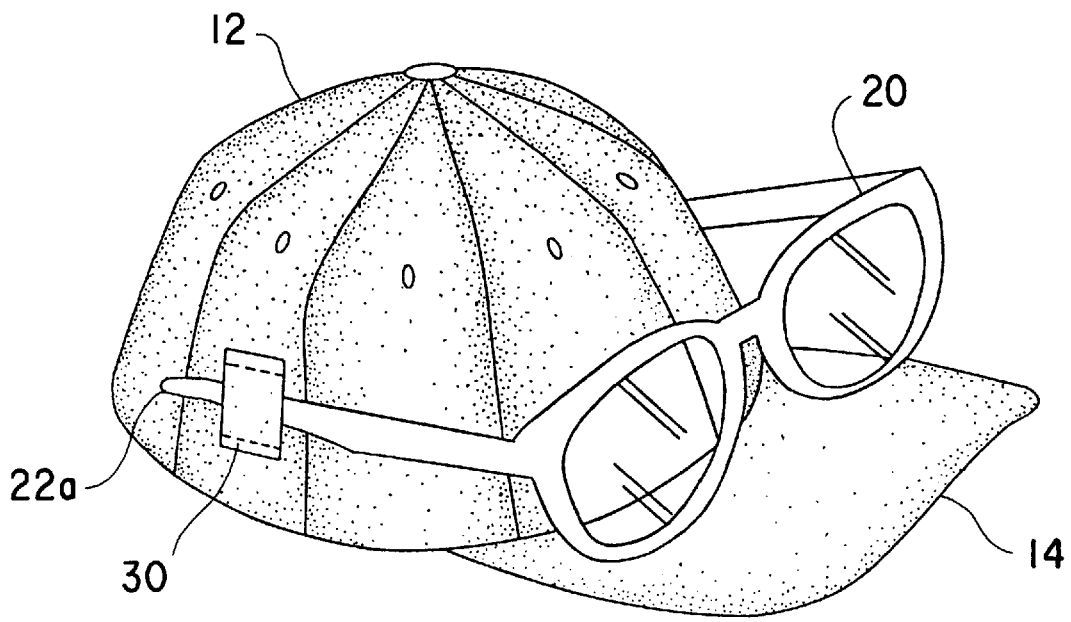
FIG. 2 is a perspective view of a hat for glasses according to a second embodiment of the present invention.
Figure 3:
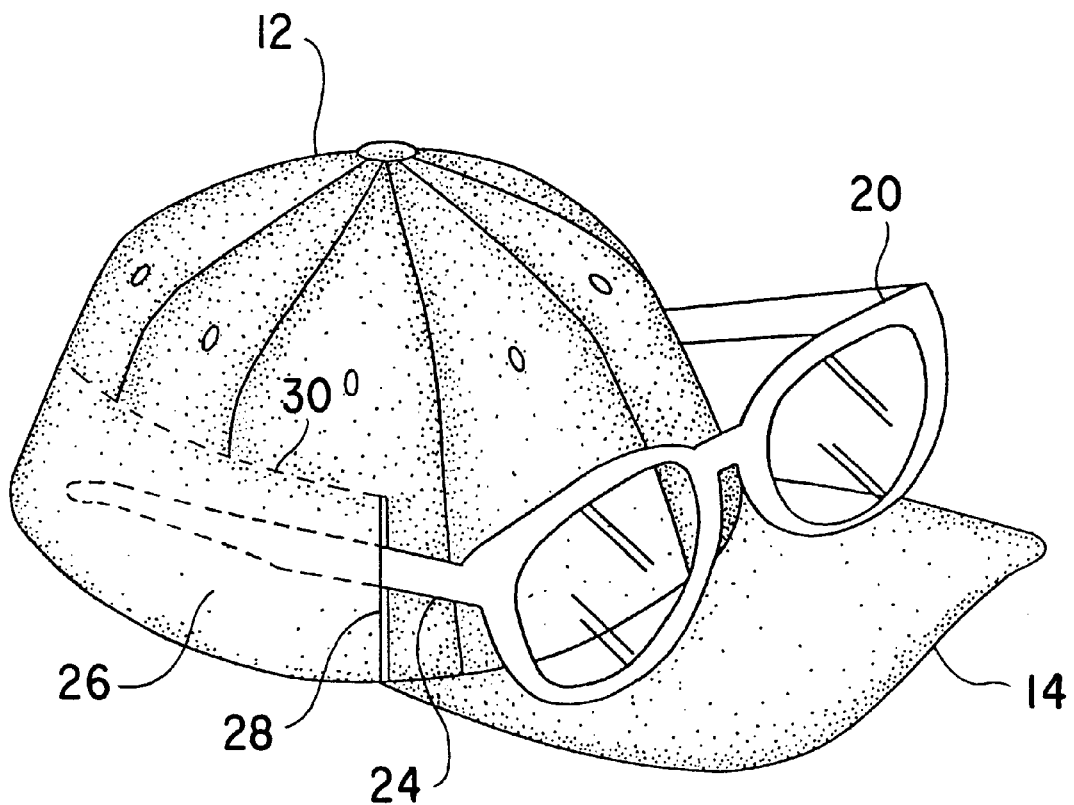
FIG. 3 is a perspective view of a hat for glasses according to a third embodiment of the present invention.

As shown in FIG. 2, a second embodiment of the instant invention employs a sleeve 30 attached to crown 12. Sleeve 30 is attached to both sides of the crown and is positioned above the visor in the same manner as buttonholes 16 and 18. Sleeve 30 may be made of the same material as crown 12 and may be color-coordinated as desired. Although usable with glasses having a curved end piece, the embodiment as illustrated in FIG. 2 has been found to be most effective when used with glasses having a straight end piece as indicated at 22*a*. Attention is now directed to FIG. 3 which illustrates an embodiment of the invention wherein the cap's conventional headband 26 is employed to secure the temple 24 of glasses 20 therein. To accomplish this, a button hole 28 is disposed on each side of the cap (only one side is shown). Button hole 28 is vertically oriented and is approximately one-half of an inch in height. Headband 26 is stitched to cap 10 from a point adjacent the top of button hole 28 to a point approximately three inches toward the rear of the cap as shown at 30. The stitched headband forms a channel for receiving and supporting the temple therein. Like the second embodiment, the instant embodiment is best suited for glasses having straight ends.

It is to be understood that the present invention is not limited to the embodiments described above, but encompasses any and all embodiments within the scope of the following claims.

I claim:

1. A baseball cap, said baseball cap comprising a crown portion, said crown portion having an interior surface, an exterior surface, a front end, a rear end and two sides;
   a visor portion attached to said crown portion at said front end and extending outwardly therefrom;
   passage means formed on each side of said crown portion, said passage means adapted to receive and support an end piece and temple of a pair of eyeglasses;
   said passage means comprising a single vertically oriented buttonhole formed in each side of said crown, each said button hole having a top and a bottom; and
   a headband positioned on said interior surface of said crown portion, said headband having an upper edge;
   said upper edge stitched to each side of said crown portion from a point adjacent the top of each said vertically oriented buttonhole to a point approximately three inches toward the rear end of said crown portion.

* * * * *